(12) United States Patent
Wiklof et al.

(10) Patent No.: US 7,375,311 B2
(45) Date of Patent: May 20, 2008

(54) SCANNED-BEAM IMAGER WITH PHASE OFFSET PHOTON EMISSION IMAGING

(75) Inventors: Christopher A. Wiklof, Everett, WA (US); Gerald Ray Apperson, Lake Forest Park, WA (US); Gregory T. Gibson, Snohomish, WA (US)

(73) Assignee: Microvision, Inc., Redmond, WA (US)

( * ) Notice: Subject to any disclaimer, the term of this patent is extended or adjusted under 35 U.S.C. 154(b) by 13 days.

(21) Appl. No.: 11/384,207

(22) Filed: Mar. 17, 2006

(65) Prior Publication Data

US 2007/0215789 A1    Sep. 20, 2007

(51) Int. Cl.
  *G02B 7/04* (2006.01)
(52) U.S. Cl. .................. 250/201.3; 250/208.1
(58) Field of Classification Search ............. 250/208.1, 250/235, 216, 559.4, 458.1, 459.1, 310, 396 R, 250/201.3, 226; 356/318, 432
See application file for complete search history.

(56) References Cited

U.S. PATENT DOCUMENTS 5,751,839 A * 5/1998 Drocourt et al. ............ 382/133
5,952,668 A * 9/1999 Baer ........................ 250/492.2

* cited by examiner

*Primary Examiner*—Que T Le
(74) *Attorney, Agent, or Firm*—Kevin D. Wills

(57) ABSTRACT

Aspects of the subject matter described herein relate to attributing light emissions to spots a light was scanned over. In aspects, the scanned light includes light capable of increasing light emissions from at least one type of matter. A detector detects emitted light that comes from spots the light was previously scanned over. Circuitry attributes emitted light with spots within the area. Data representing light that reflects from each spot may be combined with data representing light that emits (if any) from each spot to create an image. The emitted light may be assigned a false color in the image to distinguish it from reflected light in the image. Emitted light may occur as a result of fluorescent activity. Other aspects are described in the specification.

57 Claims, 10 Drawing Sheets

US 7,375,311 B2

SCANNED-BEAM IMAGER WITH PHASE OFFSET PHOTON EMISSION IMAGING

SUMMARY

Briefly, aspects of the subject matter described herein relate to attributing light emissions to spots within an area over which a scanned light was previously scanned. The scanned light includes light capable of inducing light emissions from at least one type of matter. A detector detects emitted light that comes from spots the light was previously scanned over. Circuitry attributes emitted light with spots within the area. Data representing light that reflects from each spot may be combined with data representing light that emits (if any) from each spot to create an image. The emitted light may be assigned a false color in the image to distinguish it from reflected light in the image. Emitted light may occur as a result of fluorescent activity.

This Summary is provided to briefly identify aspects of the subject matter described herein that are further described below in the Detailed Description. This Summary is not intended to identify key or essential features of the claimed subject matter, nor is it intended to be used to limit the scope of the claimed subject matter.

DETAILED DESCRIPTION

The phrase "subject matter described herein" refers to subject matter described in the Detailed Description unless the context clearly indicates otherwise. The term "includes" should be read as "includes, but is not limited to" unless the context clearly indicates otherwise. The term "or" is an inclusive "or" operator, and is equivalent to the term "and/or", unless the context clearly dictates otherwise. The term "an embodiment" should be read as "at least one embodiment." The phrases "aspects of the subject matter described herein" and "aspects" are equivalent and should be read as "at least one feature of at least one embodiment". Identifying aspects of the subject matter described in the Detailed Description is not intended to identify key or essential features of the claimed subject matter.

Flow diagrams are depicted in one or more figures below. In an embodiment, actions associated with the flow diagrams occur in an order corresponding to the flow diagrams. In other embodiments, actions are constrained only by the order in which results are required and may occur in other orders or in parallel, depending upon implementation. It will be recognized by those skilled in the art that alternative actions may be substituted for actions described herein to achieve the same function or that some actions may be omitted or changed to provide the same functionality without departing from the spirit or scope of the subject matter described herein.

Figure 1:
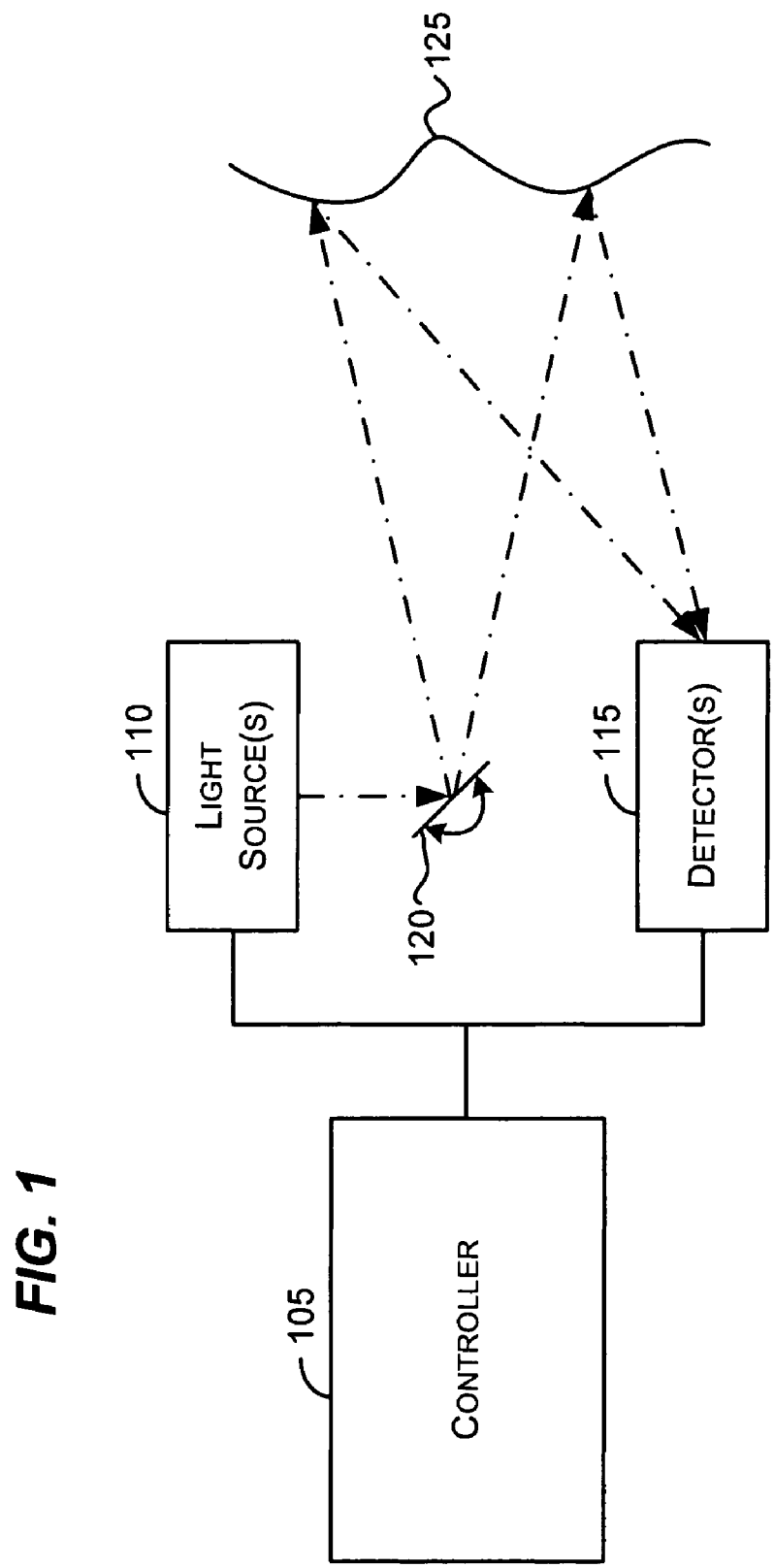
FIG. 1 is a block diagram that represents a scanned-beam system according to an embodiment.

FIG. 1 is a block diagram that represents a scanned-beam system according to an embodiment. The system includes a controller 105 coupled to one or more light source(s) 110, one or more detector(s) 115, and one or more light directing element(s) 120. According to an embodiment, the controller 105 may vary the intensity of the light source(s) 110 as well as the sensitivity of the detector(s) 115. In addition, the controller 105 may control the light directing element(s) 120 to cause the light transmitted from the light source(s) 110 to be sent to various locations of a scanning area 125. In some implementations, the light directing element(s) 120 may oscillate at a known or selectable frequency. In such implementations, the controller 105 may direct the light from the light source(s) 110 via the light directing element(s) 120 by controlling when the light source(s) 110 emit light. Light that reflects from the scanning area 125 may be detected by the detector(s) 115. The detector(s) 115 may generate data or signals (hereinafter "data") regarding the light reflected from the scanning area 125 that is sent back to the controller 105. This data may be used to generate an image frame that corresponds to the scanning area 125.

Images may be detected at a specified or selected frame rate. For example, in an embodiment, an image is detected and converted into a frame 30 times per second.

In an embodiment, light (sometimes referred to as a "light beam") comprises visible light. In other embodiments, light comprises any radiation detectable by the detector(s) 115 and may include any one or more of infrared, ultraviolet, radio, gamma waves, x-rays, and radiation of other frequencies in the electromagnetic spectrum.

Light from the light source(s) 110 may be transmitted towards the light directing element(s) 120 via an optical element such as one or more optical fibers. In an embodiment, the light source(s) 110 may generate a plurality of colored lights (e.g., red, blue, and green) that are combined to form substantially white light which is then scanned over the scanning area 125 via the light directing element(s) 120. In an embodiment, the light source(s) 110 may generate five different colored lights including red, blue, green, and light with wavelengths between red and green and green and blue. This may be used to create a 5-channel system with improved color gamut. In an embodiment, the light source(s) 110 may generate light in the infrared, ultraviolet, or other electromagnetic frequency which may be combined to form an extended spectrum system.

In an embodiment, the light source (s) 110 may generate light having various other properties. For example, two of the light source(s) 110 may generate red light differing from each other by several nanometers in wavelength. This embodiment may be used to improve discrimination of red objects, for example.

In other embodiments, light sources having therapeutic properties may be used for treatment. For example, high powered infrared lights may be used to cauterize, ultraviolet light may be used to enable phototropic drugs, etc. A combination of narrow wavelength light sources may be used to avoid exposure to unwanted wavelengths, for instance when a phototropic drug is present, but it is desired to activate it only in certain cases. Therapeutic beams may be selectively enabled by a physician or remote expert, or alternatively may be automatically enabled based on image properties. Therapeutic beams may be enabled for an entire scanning area, for a portion of the scanning area including specific, small spots within the scanning area.

In an embodiment, a light beam created from the light sources may be passed through the center of a scanning mirror, bounced off a reflector, and return to the scanning mirror, which scans (i.e., directs) it over a scanning area. This concentric beam path may be used to reduce the size of an imaging tip for use in inserting into a body cavity or other constricted area. In addition, polarization properties of the beam and the reflector may be manipulated to maximize signal strength and minimize stray light that reaches the scanning area.

Light from the beam created from the light sources 110 may be scattered by, transmitted through, absorbed by, or reflected off surfaces in the scanning area and may encounter multiple transmission paths before reaching the detector(s) 115. In an embodiment, the detector(s) 115 may comprise non-imaging detectors. That is, the detector(s) 115 may operate without the use of a lens, pin hole, or other optical device that creates an image from the detected light on a conjugate image plane. A conjugate image plane may comprise a plane upon which a lens or similar device may direct light to create an inverted image. For example, the lens of a film camera may direct light to a plane that includes a frame of the film in the camera. The light so directed forms a conjugate image on the plane that is detected by the film. As another example, a digital camera lens may direct light to an array of detectors (CCD detectors) within the camera. Again, the directed light may form an inverted image on the array of detectors and using light and spatial information associated with the detectors (e.g., how much light and of what type was received at each detector together with the location of the detector) an image may be formed.

Instead of using a conjugate image plane, the detector(s) 115 may detect light that reaches the detector(s) 115 from any path. Based on the area to which the light directing element(s) 120 were directing light at or near the time the light reaches the detector(s) 115, light detected by the detector(s) 115 may be attributed to the area in the scanning area 125 and assigned to a pixel (e.g., via the controller 105, a portion thereof, or other circuitry) and may be used (optionally, together with other detected light) to form an image (e.g., via the controller 105, a portion thereof, or other circuitry). In an embodiment, the detector(s) 115 may comprise photodiodes or other light-sensitive elements that are mounted close to the light directing element(s) 120. In other embodiments, the detector(s) 115 may comprise optical fibers that collect received light and transmit it to a remote detection unit, where it is converted into electrical signals for further processing. Such gathering fibers may be arranged circumferentially around the light directing element(s) 120, for example.

In an embodiment, the light directing element may also be used to gather light that reflects off surfaces of the scanning area. For example, light that reflects from the surface 125 or travels other paths may travel back to the light directing element 120. This light may then be directed to the detector(s) and used to construct an image. In one implementation, collection fibers may be arranged across the tip of a device transmitting light from the light sources 110. The collection fibers may be arranged in interstitial spaces between irrigation channels, working channels, and the like, for example.

The controller 105 may comprise one or more application-specific integrated circuits (ASICs), discrete components, embedded controllers, general or special purpose processors, any combination of the above, and the like. In some implementations, the functions of the controller 105 may be performed by various components. For example, the controller may include hardware components that interface with the light source(s) 110 and the detector(s) 115, hardware components (e.g., such as a processor or ASIC) that performs calculations based on received data, and software components (e.g., software, firmware, circuit structures, and the like) encoding instructions that a processor or the like executes to perform calculations. These components may be included on a single device or distributed on more than one device without departing from the spirit or scope of the subject matter described herein.

Some software components may be stored on any available machine-readable media accessible by the controller 105 and may include both volatile and nonvolatile media and removable and non-removable media. By way of example, and not limitation, machine-readable media may comprise storage media and communication media. Storage media includes both volatile and nonvolatile, removable and non-removable media implemented in any method or technology for storage of information such as machine-readable instructions, data structures, program modules, or other data. Storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the controller 105. Communication media typically embodies machine-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of machine-readable media.

The controller 105 may include or be connected to storage media and may operate in a networked environment using logical connections to one or more remote machines. A remote machine may comprise a personal computer, a server, a router, a network PC, a peer device, or other common network node. The logical connections may include a local area network (LAN) and a wide area network (WAN) and may also include other networks and may be implemented in wired, wireless, or a combination of wired and wireless technologies. Such networking environments are commonplace in offices, enterprise-wide computer networks, intranets and the Internet, for example.

In an embodiment, at least part of the scanned-beam system is part of a camera, video recorder, document scanner, endoscope, laparoscope, boroscope, machine vision camera, other image capturing device, or the like. In an embodiment, the scanned-beam system may comprise a microelectromechanical (MEMS) scanner that operates in a progressive or bi-sinusoidal scan pattern. Some exemplary scanners are described in U.S. Pat. No. 5,629,790 to Neukermanns et al., entitled MICROMACHINED TORSIONAL SCANNER. In some embodiments, the light directing element(s) 120 may be operated by a magnetic drive. In other embodiments, the light directing element(s) 120 are operated by an electrostatic drive or by a combination of a magnetic and electrostatic drives. The MEMS scanner may be a bulk micro-machined MEMS scanner or may be a surface micro-machined device.

Figure 2:
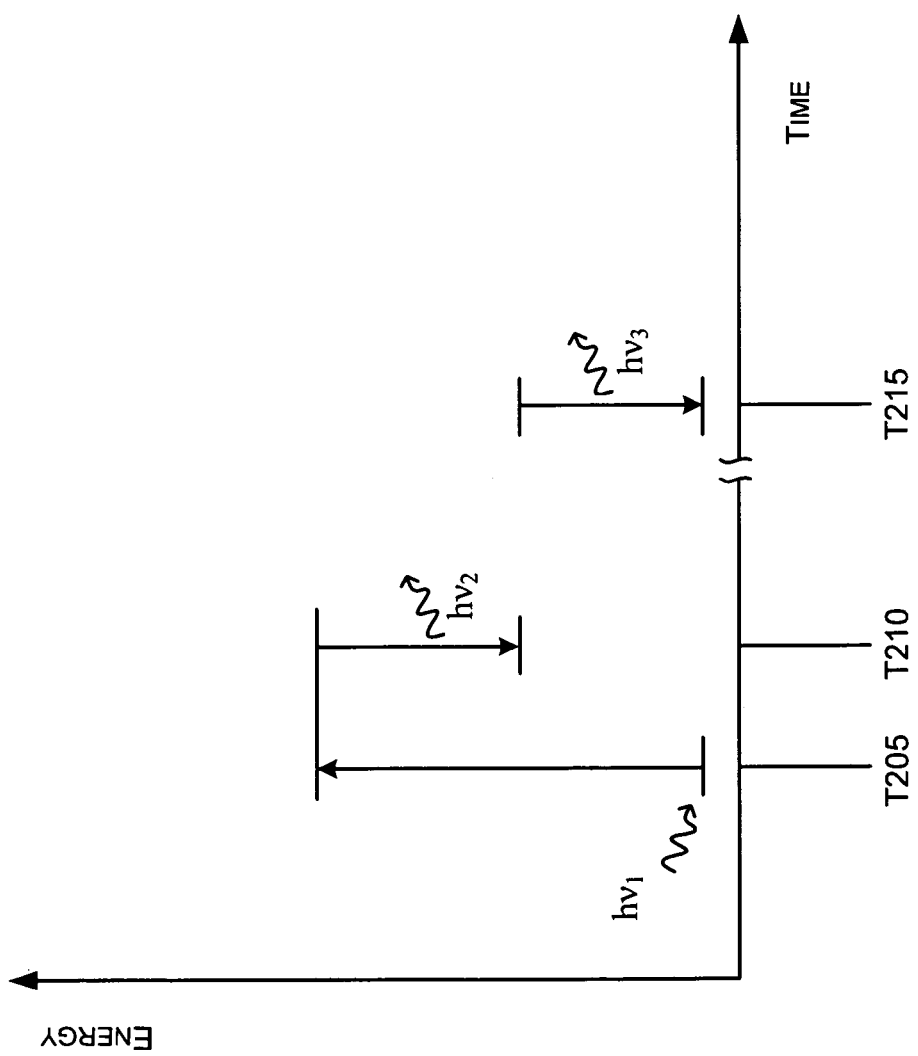
FIG. 2 is a diagram that generally represents events surrounding absorption and emission of photons according to an embodiment.

FIG. 2 is a diagram that generally represents events surrounding absorption and emission of photons according to an embodiment. When a light beam having a particular frequency comes in contact with material that absorbs light with that frequency, some of the energy of the light beam may be absorbed by the material. On a molecular or atomic level, absorption may be viewed as an electron receiving energy by absorbing a photon and moving from a lower energy state to a higher energy state in response to absorbing the photon. If the absorbed light has a frequency $v_1$, then the corresponding photon will have energy of $hv_1$, where h represents Planck's constant and $v_1$ represents the frequency of the absorbed light. Referring to FIG. 2, an electron may absorb a photon at time T205. In some materials (e.g., fluorescent materials), a statistically predictable period after absorption, the electron may move to a lower energy state and in doing so emit another photon. Emitting a photon after a characteristic time delay from absorption of a photon in response to moving to a lower energy state is sometimes called a "fluorescent response". Note that the electron may not always emit a photon when moving to a lower energy state. When it does emit a photon, however, the emitted photon may have energy of $hv_2$ where $hv_2<hv_1$. Because h is a constant, this implies that light that corresponds to the emitted photon has a longer wavelength than the wavelength of the absorbed light.

Returning to FIG. 2, emitting a photon may occur, for example, at time T210. At a later time (e.g., T215) which may be much later relative to the difference between T205 and T210, the electron may move to its original energy state and may emit yet another photon having energy of $hv_3$. This process may repeat as the electron absorbs and emits photons.

When the energy of the emitted photon is less than the energy of the absorbed photon, this is sometimes referred to herein as a down-converting transition. As will be seen from the discussion in conjunction with FIG. 3, it is also possible to have the emitted photon have more energy than an absorbed photon. This is sometimes referred to herein as an up-converting or two-photon transition.

Figure 3:
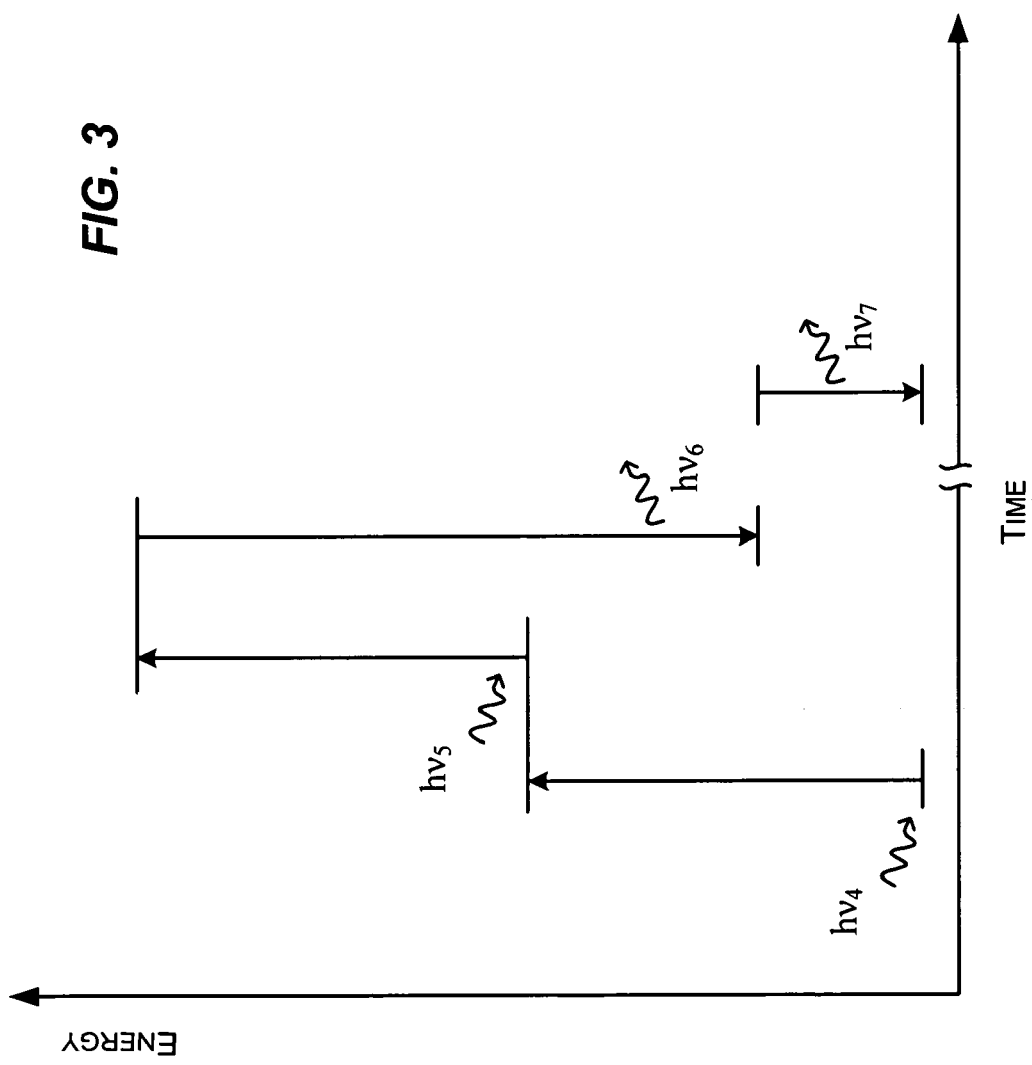
FIG. 3 is a diagram that generally represents events surrounding absorption and emission of photons according to an embodiment.

FIG. 3 is a diagram that generally represents events surrounding absorption and emission of photons according to an embodiment. In FIG. 3, an electron absorbs two photons at times T305 and T310 before emitting a photon at time T315. The first emitted photon may have more energy ($hv_6$) than either of the absorbed photons but have less energy than the combined energies ($hv_4+hv_6$) of the absorbed photons. Some time after emitting the first photon (e.g., at time T320), the electron may move to its original energy state and may emit yet another photon having energy of $hv_7$. Alternatively, or in addition to emitting a photon, the electron may cause heat, vibrational, or some other type of energy when moving to its original energy state.

Returning to FIG. 1, to distinguish emitted light from reflected light, filters may be coupled to or comprise the detector(s) 115. Each filter may allow light from a range of frequency to pass through the filter or may prevent light from a range of frequencies to pass through the filter. For example, some filters may allow red, green, or blue light to pass through them while another filter may allow emitted light having an anticipated wavelength corresponding to emission expected based on an excitation beam. As described in conjunction with FIGS. 2 and 3, emitted light may have a longer or shorter wavelength than the light which causes the excitation. Some emitted light may fall in the infrared spectrum or lower frequency spectrum, some may fall into the visible spectrum, and other emitted light may fall in the ultraviolet spectrum or higher frequency spectrum. The ranges (e.g., shorter wavelengths and longer wavelengths) that may be emitted may depend on the characteristics of the material.

In an embodiment, reflected or scattered light detection generally occurs simultaneously with illumination, ignoring light propagation velocity. In contrast, fluorescent light is emitted, and consequently detected, after a delay. The delay may be treated as a phase offset from excitation of the spot or receipt of reflected light from the spot.

Figure 4:
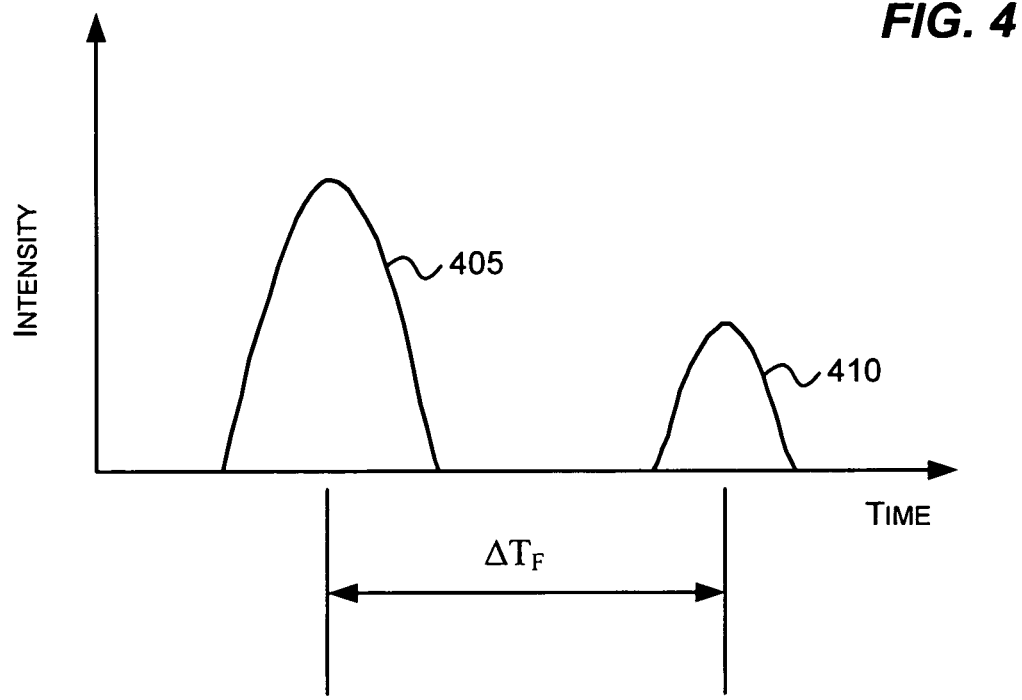
FIG. 4 is a diagram that generally illustrates a characteristic time offset $\Delta T_F$ between a photonic excitation signal 405 and a response signal 410 according to an embodiment.

FIG. 4 is a diagram that generally illustrates a characteristic time offset $\Delta T_F$ between a photonic excitation signal 405 and a response signal 410 according to an embodiment. The excitation signal 405 may correspond to light of a first wavelength while the response signal 410 may correspond to light that is emitted at a generally longer wavelength. For fluorescent emissions, the time offset $\Delta T_F$ between excitation and emission generally ranges from nanoseconds to milliseconds, with many systems showing a characteristic time offset in the range of microseconds.

Some cellular structures emit photons when excited by photons of a light beam with appropriate frequency. In particular, cancer cells and other irregular or abnormal cells may respond in this fashion to light (perhaps of a non-visible frequency) that regular cells do not respond to. This may be useful for detecting abnormal cells via the use of a scanned-beam system. For example, a scanned-beam system may emit light that abnormal cells are more likely to absorb. Such cells may thereafter emit photons that may be detected by the scanned-beam system. Because the detected photons may be emitted and received at a later time than when photons were sent to a particular area of a scanned area, the time delay between sending an excitation photon and the response photon may be used to associate the received light with the area the scanned-beam system was sending light to that caused the response photon. Some cells and other materials have a well-known range of response times at which response photons are sent in response to excitation photons.

Fluorescent material may be attached to a molecule that attaches to specific tissue including cellular structures, bacteria, viruses, and the like. When light of an appropriate frequency is directed to an area including the tissue, a fluorescent response in the form of emitted light may occur. Fluorescent material may also be attached to other molecular structures through the use of a carrier that carries the fluorescent material and binds to the other molecular structures. Light of an appropriate frequency may also cause a fluorescent response that may be used to identify locations including the other molecular structures.

Figure 5:
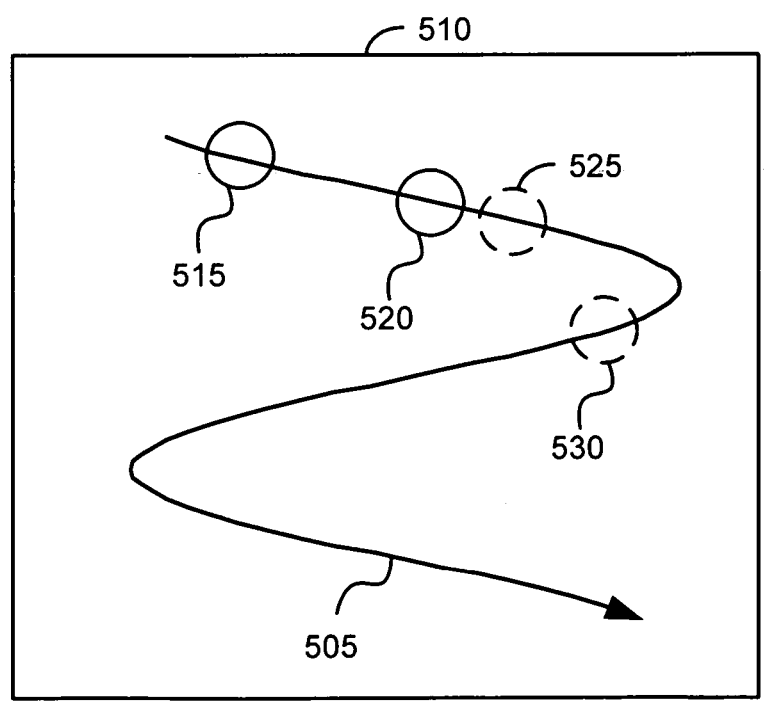
FIG. 5 illustrates an exemplary partial scan path 505 of a light beam of a scanned-beam system over a scan area 510 according to an embodiment.

FIG. 5 illustrates an exemplary partial scan path 505 of a light beam of a scanned-beam system over a scan area 510 according to an embodiment. A first illumination spot 515 represents a beam location of a first spot illuminated at a first instant in time. A second illumination spot 520 represents a beam location of a second spot illuminated at a second instant in time. A phantom spot 525 illustrates a beam location when emission from the first illuminated spot 515 is received by a detector. A phantom spot 530 illustrates a beam location when a photon emission from the second illuminated spot 520 is received by the detector. As may be appreciated from the Figure, to construct an image from the received photons, the scanned-beam system may compensate for the offset between excitation and emission in order to assign received emissions to the locations corresponding to the areas to which light was directed that caused the emissions. Furthermore, such an image may be combined with reflected light images (e.g., images of the same scan area 510) obtained from light that reflects from the scan area 510) to aid the viewer in manipulating tools, diagnosing or analyzing structures within the scan area 510, or otherwise interacting with material (e.g., cell tissue) in the scan area 510. In combining a reflected light image with data obtained from delayed emissions, one or more false colors may be assigned to the delayed emissions to indicate where the emissions occurred in the image.

Figure 6:
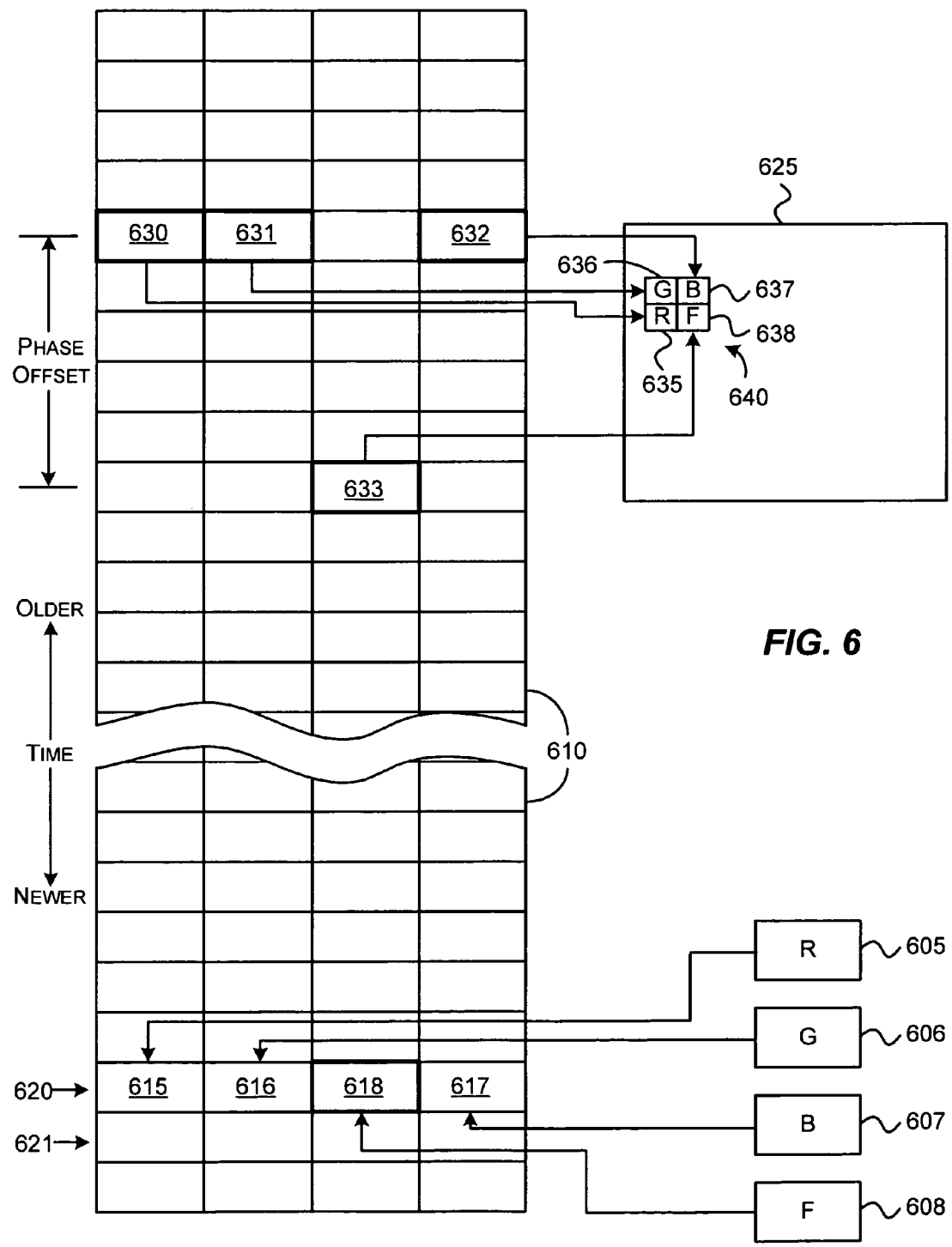
FIG. 6 illustrates a mechanism for constructing an image with phase offset in the fluorescence channel according to an embodiment.

FIG. 6 illustrates a mechanism for constructing an image with phase offset in the fluorescence channel according to an embodiment. The detector(s) 115 of FIG. 1 may be divided into or light from the detector(s) 115 may be provided to red, green, blue, and fluorescence detection subsystems 605, 606, 607, and 608, respectively. Each of the subsystems 605-608 may provide a signal corresponding to the amounts of red, green, blue, and fluorescent light detected at an instant in time. Digital values corresponding to these signals may be written into an input buffer 610 at respective memory locations 615-618. Input buffer 610 may be organized to store data in a time sequence in the vertical axis as shown. After storing the digital values in a row (e.g., row 620) of the buffer 610, pointers, counters, or the like may be incremented so that the next row (e.g., row 621) may be used for storing values corresponding to the signals generated by the subsystems 605-608 during a next period of time. This period of time may correspond to a sampling time and may depend on the number of pixels to be sampled to create an image and the number of images per second to be created.

Although the structure of the input buffer 610 as shown in FIG. 6 has elements that correspond to rows, columns, and data locations, it will be recognized that other memory structures including linked lists, arrays with one or more dimensions, bitmaps, other memory structures, and the like may be used and that the format or contents of the structure may change without departing from the spirit or scope of subject matter described herein.

In creating an image, values may be read from the input buffer 610 to an output buffer 625. The output buffer 625 may be organized as a spatial array of pixel locations 640 corresponding to an image of the scanned area. Since the scan path 505 is known, the time sequence of values in the input buffer 610 may be written to a corresponding spatial sequence of values in the output buffer.

In creating the output buffer 625, a red value may be read from the input buffer location 630 to the output buffer location 635, a green value may be read from input buffer location 631 to output buffer location 636, and a blue value may be read from input buffer location 632 to output buffer location 637 as shown. Since the R, G, and B channels correspond to reflected light that arrives substantially simultaneously with illumination, they may all be read from the same row of the input buffer. A fluorescence value, however, may be read from a different (e.g., newer or more recent) row of the input buffer 610 (e.g., location 633) to the output buffer location 638. Thus, the output buffer location 638 corresponds to a different instant in time from the output buffer locations 635-637, but corresponds to the same pixel. The number of rows between the RGB input buffer values at 630, 631, and 632 and the F input buffer value 633 may correspond to the characteristic fluorescence time offset $\Delta T_F$ (e.g., phase offset) divided by the time allowed for entering data into each row (i.e., before changing to the next row) of the input buffer 610. The time allowed for entering data into each row may correspond to a period of a pixel clock, for example. In an embodiment, a period of a pixel clock is 20 nanoseconds. The pixel clock period may be constant or variable.

In an embodiment, the time between rows may be held constant while the pixel clock is variable. This may be accomplished, for example, by skipping rows during periods where the pixel clock is relatively slow and filling in all rows during periods where the pixel clock is relatively fast.

The composite pixel 640 may then be subsequently displayed with RGB values driving corresponding RGB pixels and the F value providing an additive value to one or more of the RGB channels to produce a false color image of the fluorescence.

Referring back to FIG. 5, the RGB values in respective input buffer locations 630, 631, and 632, and hence written into respective output buffer locations 635, 636, and 637, correspond to a pixel while the beam is located at spot 515. Conversely, the F value in input buffer location 633 corresponds to a pixel while the beam is located at 525. However, because of the characteristic fluorescence time offset $\Delta T_F$, the light received while the beam is at position 525 corresponds to light emanating from location 515.

In another embodiment, data corresponding to signals received from the fluorescence subsystem 608 may be offset during writing such that it is collocated with data corresponding to the signals received from the red, green, and blue subsystems 605-607. That is, the data may be placed correctly temporally on writing into the input buffer 610 based on the characteristic fluorescence time offset $\Delta T_F$ such that each fluorescence value appears on the same row as values for other channels that were written in response to reflected light detected when the beam was illuminating the area that caused the fluorescence to occur. For example, referring to FIG. 5, values corresponding to reflected light received from illuminating spot 515 and the fluorescent emission resulting from illuminating spot 515 may be collocated on the same row, even though the fluorescent emission occurred at some time after the beam was directed to spot 515 (e.g., when the beam was directed to phantom spot 525). When this is done, an output buffer 625 may be created by obtaining the RGB and fluorescent values from the same row.

Figure 7:
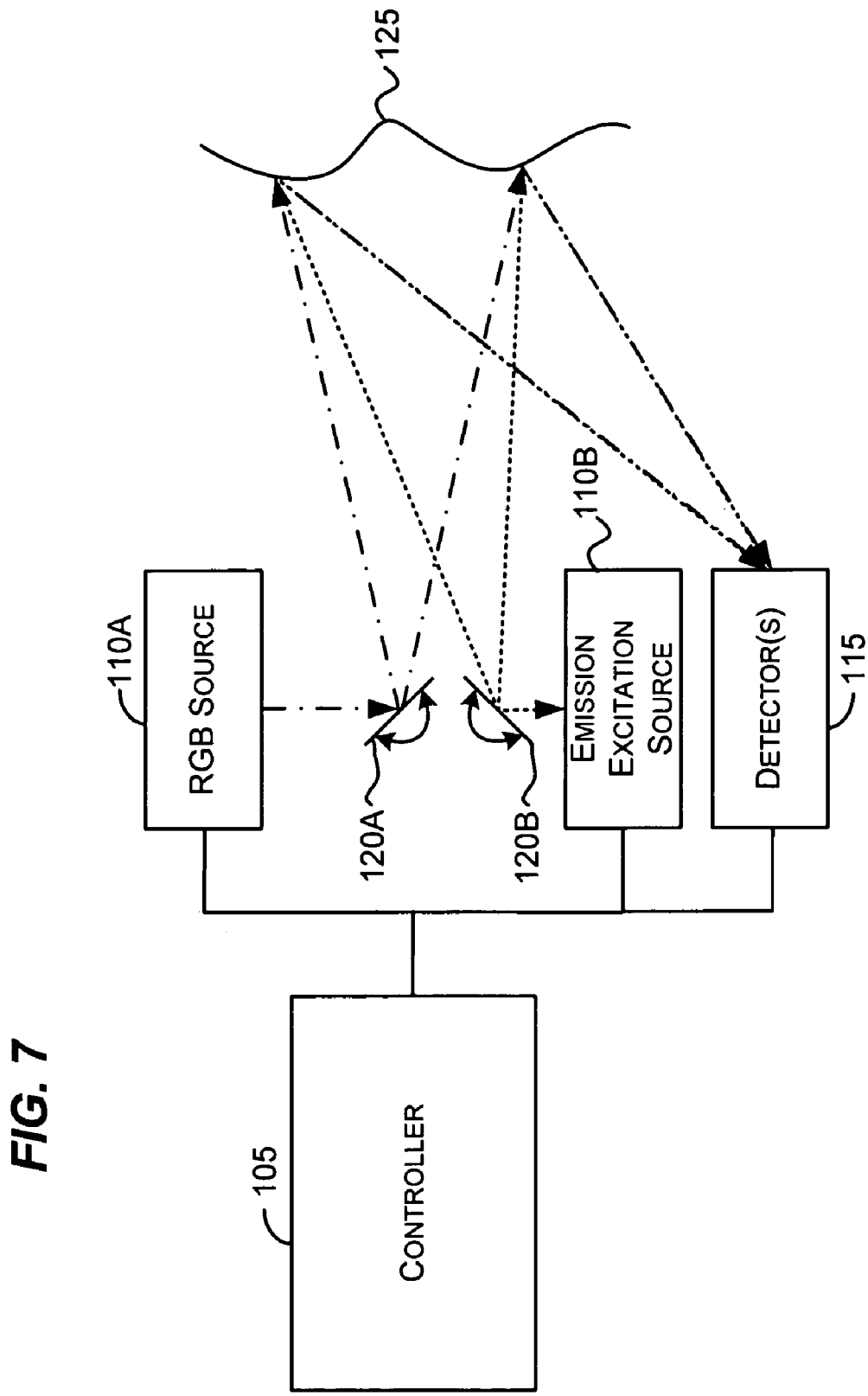
FIG. 7 is a block diagram that represents a scanned-beam system with an RGB light source 110A spatially offset from an emission excitation source 110B for scanning systems having a substantially constant fast scan velocity according to an embodiment.

FIG. 7 is a block diagram that represents a scanned-beam system with an RGB light source 110A spatially offset from an emission excitation source 110B for scanning systems having a substantially constant fast scan velocity according to an embodiment. The light sources include an RGB light source 110A and an emission excitation source 110B. The light sources function similarly to that described for light source 110 of FIG. 1. A difference is that RGB source 110A provides light that, for the most part, reflects from or is absorbed by surface area 125 without producing later photon emissions while emission excitation source 110A provides light at a frequency that, at least in part, causes absorption and emission of photons from the material that comprises the surface area 125.

The light sources 110A and 110B may launch respective beams toward a single scanner 120 at different angles. For systems with substantially constant and unidirectional fast- and/or slow-scan velocity, the respective beam launch angles may be selected such that reflecting illumination is received and reflected from a spot just as light is emitted from the spot responsive to previously received excitation light.

For embodiments with non-constant and/or bidirectional fast- and/or slow-scan velocity, light sources 110A and 110B may be respectively scanned by separate scanners 120A and 120B. By directing the light from the two light sources via their respective light directing elements (e.g., light directing element 120A and light directing element 120B) and offsetting the time at which the two light sources cause light to hit spots on the surface area 125, light that reflects from each spot together with photons that are emitted from the spot may arrive approximately simultaneously (e.g., within a fraction of a pixel period of each other) at the detector(s) 115. In such a system, performing a later temporal offset to superimpose colors representing emission light with colors of reflected light may not be needed as the emitted and reflected light arrive at the detector(s) 115 approximately simultaneously.

Figure 8:
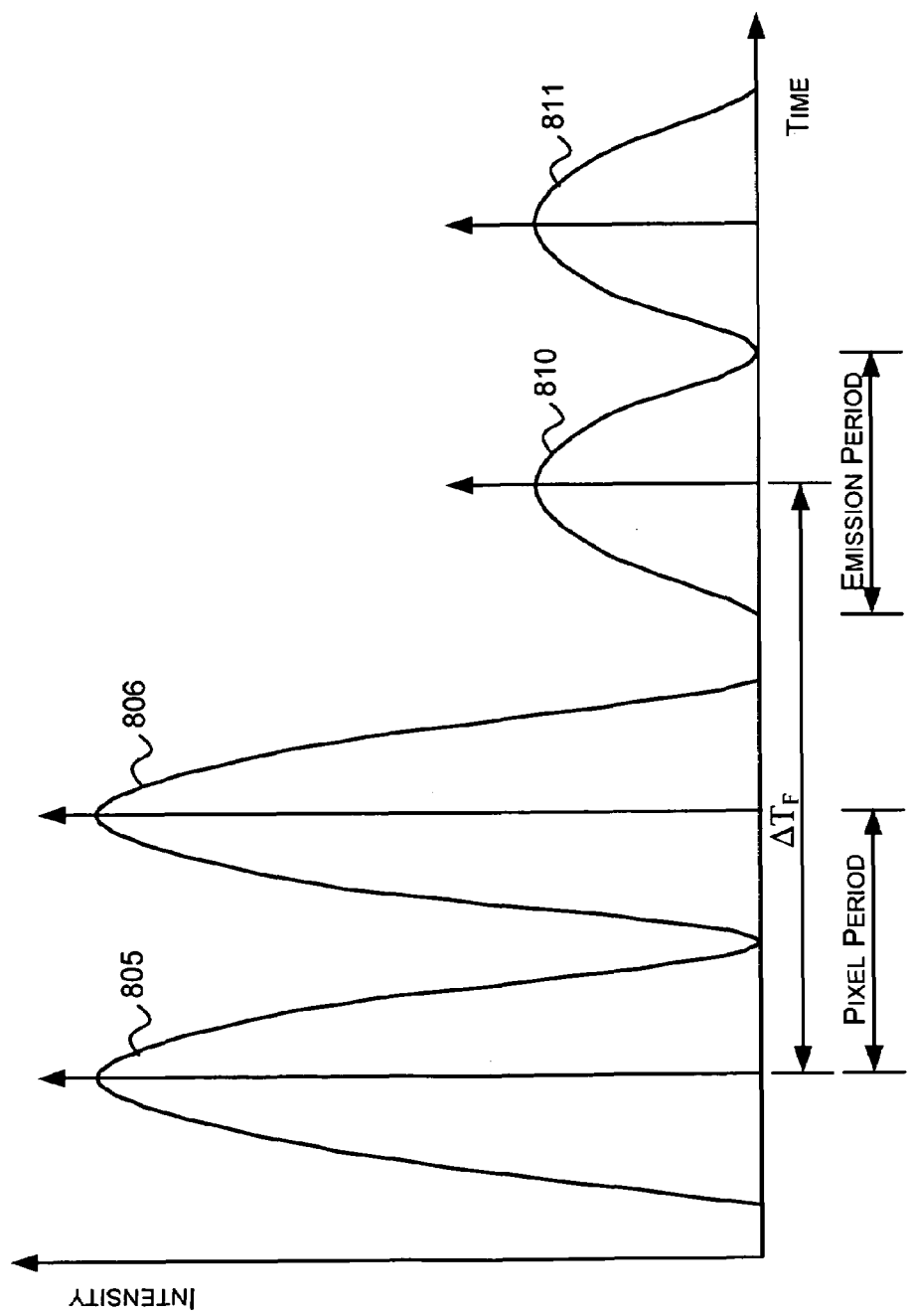
FIG. 8 is a diagram that generally illustrates the effect of emission periods that are less than the pixel period according to an embodiment.

FIG. 8 is a diagram that generally illustrates the effect of emission periods that are less than the pixel period according to an embodiment. Excitation signals 805-806 may be sent every pixel period. As long as the emission period of each emission is less than the pixel period, emissions may be correctly associated with specific excitation signals. Based on the previous discussion, this allows the scanned-beam system to attribute light detected from the emissions to the appropriate spots of the scanned area. Unfortunately, not all emissions may decay in intensity as quickly as those shown in FIG. 8.

Figure 9:
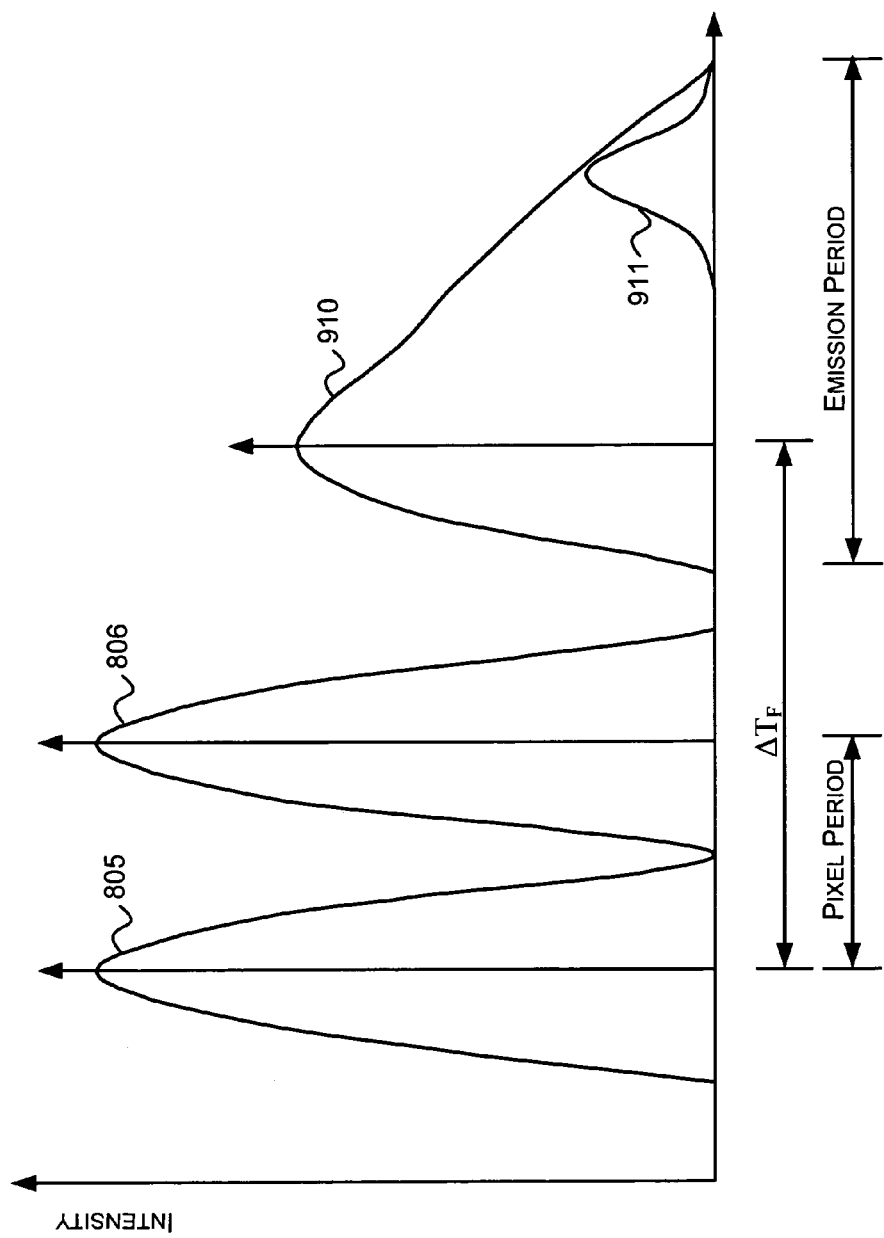
FIG. 9 is a diagram that generally illustrates the effect of an emission period that is greater than the pixel period according to an embodiment.

For example, referring to FIG. 9, which is a diagram that generally illustrates the effect of an emission period that is greater than the pixel period according to an embodiment, it can be seen that when the emission period of any particular emission is greater than the pixel period that emissions may no longer be correctly attributed to specific excitation signals. In particular, the emission 910 may contribute to the light detected for two or more pixels. This may cause, for example, the detected signal corresponding to emission 911 to include a combination of light from emissions 910 and 911.

One way to deal with this is to allow the emission from one spot to be attributed to two or more pixels. This may involve summing emissions that may occur simultaneously even though they come from different spots. One result of such an approach is to accept somewhat reduced resolution of fluorescence images compared to reflected light images. Another mechanism for dealing with this is to increase the length of the pixel period. This may decrease the resolution or may decrease the number of images per second that may be obtained at a given resolution in both fluorescence and reflected light images. Yet another mechanism may involve determining a decay rate based on part or all of the curve of each emission that falls within a pixel period and extrapolating a curve that approximates the decay rate over the next one or more pixels, if needed. If the next pixel period also includes emission from another spot, the extrapolated curve may be subtracted from the combination of emissions to obtain the emission attributable to the other spot.

Figure 10:
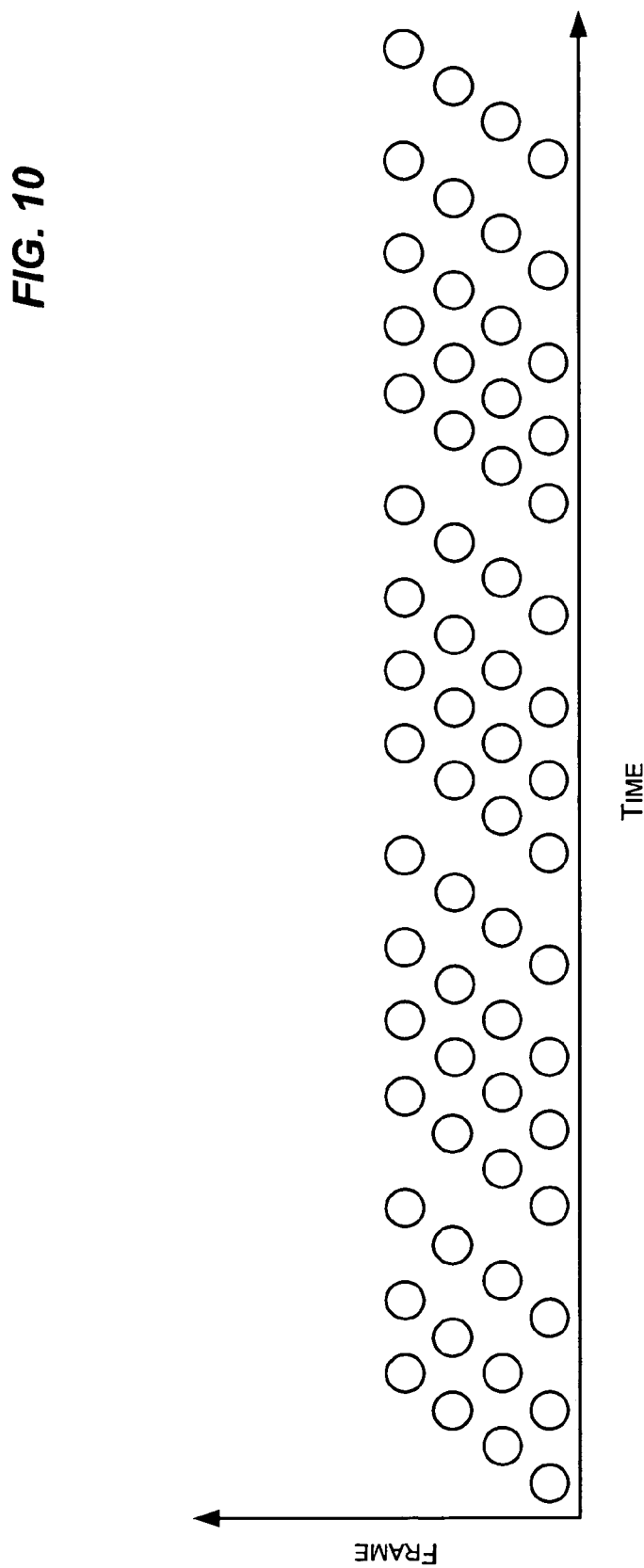
FIG. 10 is a diagram showing a varying excitation pulse pattern according to an embodiment.

In another mechanism, a varying excitation pattern may be used as described in conjunction with FIG. 10, which is a diagram showing a varying excitation pulse pattern according to an embodiment. Each of the circles in FIG. 10 corresponds to a pulse of an excitation beam. Excitation beams may be separated by one or more pixel periods to allow for longer emission periods. The light directing element directing the excitation beams may follow the path shown in FIG. 5, a raster-based pattern (e.g., scanning from left to right, scanning left, scanning right again, and so on), a bi-sinusoidal pattern, or any other pattern that covers or substantially covers the area, but may cause excitation pulses at varying times as indicated in FIG. 10 where each row corresponds to a frame (and not all pulses for the frame are shown). By appropriately spacing the pulses, commingling of emissions caused by different pulses may be avoided or reduced.

In an embodiment, the pattern of pulses is shifted from frame to frame so that spots that were not pulsed during a previous scan are scanned at a later time as the pattern of pulses eventually covers all areas in a scan area. In another embodiment, the emissions from a previous frame are used to determine where to pulse in a subsequent frame. If emissions occur in spatially adjacent areas, pulses for those areas on the next scan may be separated by a greater distance to determine whether one area caused all the emission or whether some combination of the areas caused the emission. If emission does not occur in spatially adjacent areas, the time between pulses in those areas may be reduced.

In an embodiment, the time between pulses varies randomly or according to a pattern operative to self-calibrate the fluorescence response period $\Delta T_F$. The timing of a detected pattern may thus be matched to the corresponding (earlier) illumination pattern to automatically determine one or more appropriate phase offsets. In addition, the upper and lower limit of time between pulses may be manually or automatically selected. For example, a user of the scanned-beam system may have a dial, computer, or other input device by which the user may adjust the upper and lower limit of time between pulses. An upper limit may be automatically selected by scanning an area several times starting with relatively long spaces between pulses and measuring the longest continuous emission. A lower limit may be selected as the pixel period.

In an embodiment, during an initial phase, pulses may be provided with little or no time between pulses until emission is detected. After emission is detected, the time between pulses may be increased as needed to correctly attribute emissions from different pulses.

Figure 11:
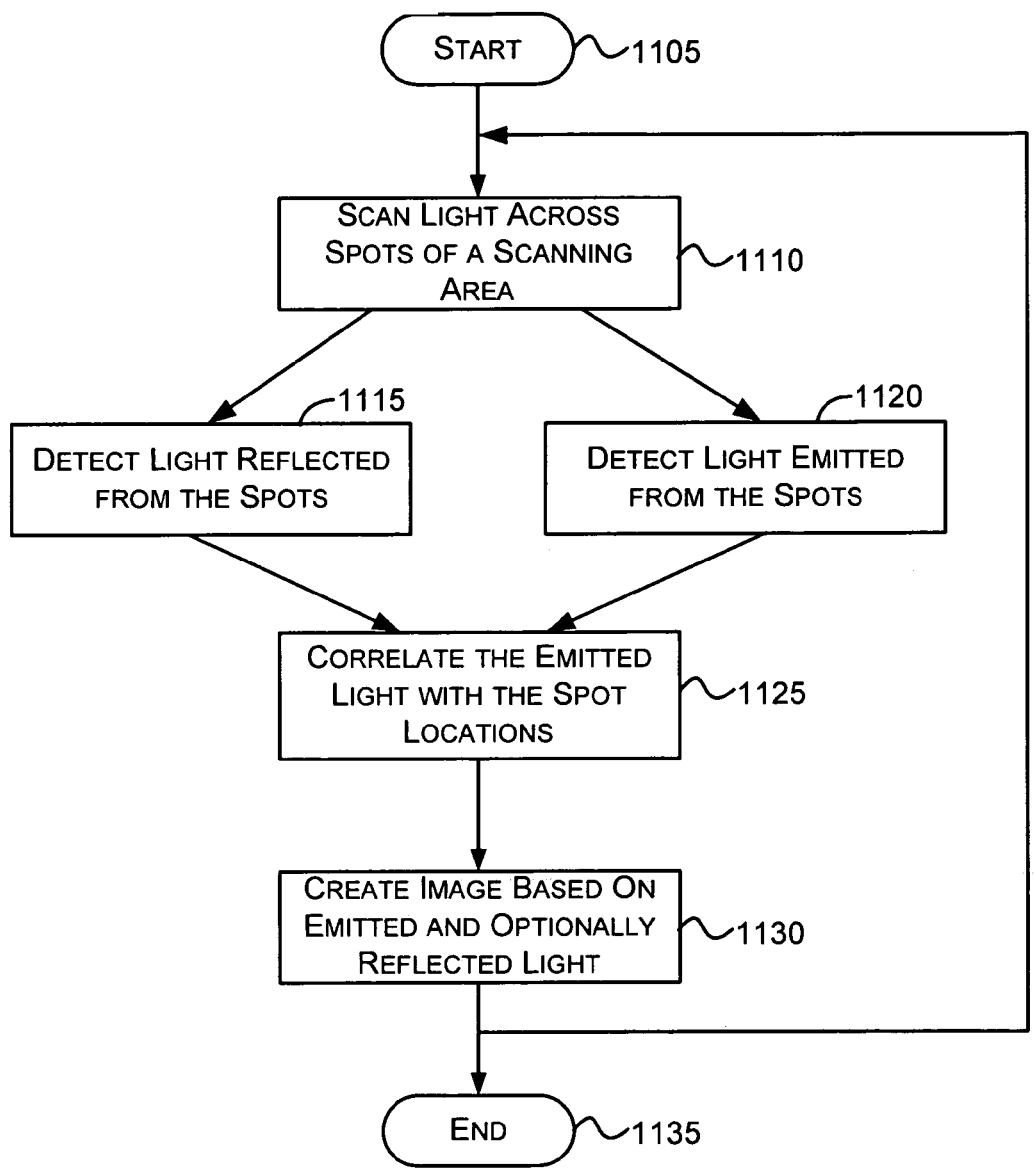
FIG. 11 is a flow diagram that generally represents actions that may occur in obtaining images according to an embodiment.

FIG. 11 is a flow diagram that generally represents actions that may occur in obtaining images according to an embodiment. At block 1105, the actions start.

At block 1110, light is scanned over spots of a scanning area. As mentioned previously, this may be done in a pattern. The pattern may be such that it covers all or most of a scanning area.

Concurrent with scanning light over spots of a scanning area, reflected light and emitted light is detected at blocks 1115 and 1120. As mentioned previously, detected emitted and reflected light for a given spot may be received together or may be offset from each other by a delayed emission time characteristic of the matter emitting the light.

At block 1125, the emitted light is correlated with the spot locations. In implementations where two lights are scanned over the area out of phase such that reflected and emitted light from each spot reaches the detectors at approximately the same time (e.g., within a pixel period or each other), correlation may comprise collocating (i.e., placing together) data corresponding to the reflected and emitted light. Collocated related reflections and emissions may also be done when reflected and emitted light arrives out of phase. Collocating may also comprise combining data that represents reflected light with data that represents emitted light together in a frame buffer or other buffer, even if the data representing the reflected light and the data representing the emitted light are not stored in contiguous memory.

Correlating emitted light may comprise using a characteristic time offset between photonic excitation and emission together with information regarding scan rate (i.e., the speed at which light is scanned in a pattern over an area) and current scan position to determine the spot corresponding to where the scan beam was when the photonic excitation occurred.

At block 1130, an image may be created based on emitted and reflected light. The image may combine data obtained from reflected light for each spot with data obtained for emitted data for each spot (if any). Emitted light may be represented using a false color.

After block 1130, if another scan is desired, the actions may continue at block 1110; otherwise, at block 1135, the actions end. The actions may be repeated for each frame of an image. Additionally, as described above, the response 1130 of one frame may be used to determine a pattern of scanning or illumination 1110 performed during a subsequent frame.

Those skilled in the art will recognize that the state of the art has progressed to the point where there is often little distinction between hardware and software implementations of aspects of the subject matter described herein. The use of hardware or software is generally (but not always, in that in certain contexts the choice between hardware and software can become significant) a design choice representing cost vs. efficiency tradeoffs. Those having skill in the art will appreciate that there are various vehicles by which processes, systems, or other technologies described herein may be implemented (e.g., by hardware, software, or firmware), and that the preferred vehicle may vary with the context in which the processes, systems, or other technologies are deployed.

For example, if an implementer determines that speed and accuracy are paramount, the implementer may opt for a mainly hardware or firmware vehicle; alternatively, if flexibility is paramount, the implementer may opt for a mainly software implementation; or, yet again alternatively, the implementer may opt for some combination of hardware, software, or firmware. Hence, there are several possible vehicles by which the processes, devices, or other technologies described herein may be implemented, wherein the vehicle to be utilized is a choice dependent upon the context in which the vehicle will be deployed and the specific concerns (e.g., speed, flexibility, or predictability) of the implementer, any of which may vary. Those skilled in the art will also recognize that an embodiment involving optics may involve optically-oriented hardware, software, or firmware.

The foregoing detailed description has set forth aspects of the subject matter described herein via the use of block diagrams, flow diagrams, or examples. Insofar as such block diagrams, flow diagrams, or examples are associated with one or more actions, functions, or operations, it will be understood by those within the art that each action, function, or operation or set of actions, functions, or operations associated with such block diagrams, flowcharts, or examples may be implemented, individually or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will also recognize that aspects of the subject matter described herein, in whole or in part, can be equivalently implemented in standard integrated circuits, as one or more computer programs running on one or more computers, as one or more programs running on one or more processors, as firmware, or as virtually any combination thereof, and that designing the circuitry or writing the code for the software and or firmware would be well within the skill of one of skill in the art in light of this disclosure. In addition, those skilled in the art will appreciate that aspects of the subject matter described herein are capable of being distributed as a program product in a variety of forms, and that an illustrative embodiment of the subject matter described herein applies equally regardless of the particular type of machine-readable media used to actually carry out the distribution.

In a general sense, those skilled in the art will recognize that the aspects described herein which may be implemented, individually or collectively, by a wide range of hardware, software, firmware, or any combination thereof may be viewed as being composed of various types of "circuitry." Consequently, as used herein "circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out aspects of the subject matter described herein, or a microprocessor configured by a computer program which at least partially carries out aspects of the subject matter described herein), electrical circuitry forming a memory device (e.g., forms of random access memory), and electrical circuitry forming a communications device (e.g., a modem, communications switch, or optical-electrical equipment).

As can be seen from the foregoing detailed description, there is provided aspects for obtaining images. While the subject matter described herein is susceptible to various modifications and alternative constructions, certain illustrated embodiments thereof are shown in the drawings and have been described above in detail. It should be understood, however, that there is no intention to limit the claimed subject matter to the specific aspects described herein, but on the contrary, the intention is to cover all modifications, alternative constructions, and equivalents falling within the spirit and scope of the subject matter, described herein.

What is claimed is:

1. An apparatus for obtaining images, comprising:
   a photon directing element operable to scan photons over an area, wherein the photons include excitation photons that are capable of increasing a probability of photon emissions from matter disposed in the area;
   a detector operable to detect an emitted photon that comes from a spot the photons were previously scanned over, wherein the spot is within the area; and circuitry operable to attribute the emitted photon to the spot.

2. The apparatus of claim 1, wherein the emitted photon results from fluorescent activity within the matter.

3. The apparatus of claim 1, wherein the emitted photon has a higher energy than an excitation photon absorbed by matter that emitted the emitted photon.

4. The apparatus of claim 1, wherein the emitted photon has a lower energy than an excitation photon absorbed by matter that emitted the emitted photon.

5. The apparatus of claim 1, wherein the emitted photon has an energy level different than photons that comprise visible light.

6. The apparatus of claim 1, wherein the emitted photon has an energy level corresponding to photons that comprise visible light.

7. The apparatus of claim 1, wherein the detector includes a non-imaging detector.

8. The apparatus of claim 7, wherein the emitted photon results from an excitation photon that was absorbed by matter within the spot, and wherein the circuitry is operable to determine a time at which the excitation photon was sent from the photon directing element based on a characteristic time delta between absorption and emission of photons from matter within the spot.

9. An apparatus for obtaining images, comprising:
a light directing element operable to scan a light including a first wavelength over an area, wherein the first wavelength is capable of inducing delayed emission of a second wavelength from matter disposed in the area;
a detector operable to detect the second wavelength emitted from a spot the light was previously scanned over, wherein the spot is within the area; and
circuitry operable to attribute the second wavelength to the spot.

10. The apparatus of claim 9, wherein the second wavelength is longer than the first wavelength.

11. The apparatus of claim 10, wherein the second wavelength is shorter than the first wavelength.

12. The apparatus of claim 10, wherein the first wavelength is capable of inducing emission of the second wavelength after a characteristic delay.

13. The apparatus of claim 12, wherein the circuitry is further operable to determine the characteristic delay and determine a location corresponding to the spot based on the characteristic delay.

14. An apparatus for obtaining images, comprising:
a first photon directing element operable to scan first photons over an area, the first photons including an excitation photon that increases a probability of an emitted photon from matter disposed in the area that is responsive to the excitation photon, wherein the emitted photon has an energy level that is different from the excitation photon;
a second photon directing element operable to scan second photons over the area, the second photons including photons corresponding to visible light to reflect from matter within the area;
a detector operable to detect photons;
circuitry operable to attribute an emitted photon to a spot the first photons were previously scanned over, wherein matter within the spot emitted the emitted photon; and
circuitry operable to construct an image corresponding to reflected and emitted photons that come from the area.

15. The apparatus of claim 14, wherein the matter that is responsive to the excitation photon is structured to absorb the excitation photon and to emit the emitted photon, if emitted, after a predictable time interval when returning to a more stable state.

16. The apparatus of claim 14, wherein the matter that is responsive to the excitation photon comprises fluorescent matter.

17. The apparatus of claim 14, wherein the excitation photon has an energy level that increases a probability of delayed photon emission, relative to photon absorption, of at least a selected type of matter.

18. The apparatus of claim 14, wherein the first photon directing element is further operable to scan the first photons over the area ahead of the second photons scanned by the second photon directing element such that emitted and reflected photons from the spot arrive at the detector within a period corresponding to a sampling time.

19. The apparatus of claim 14, wherein the first and second photon directing elements are operable to scan light over the area approximately in unison such that emitted photons for the spot are detected by the detector after reflected photons for the spot are detected by the detector.

20. The apparatus of claim 14, wherein the second photons include photons having energy levels corresponding to energy levels of photons in red, blue, and green light.

21. The apparatus of claim 14, wherein the first photons include photons of an energy level capable of inducing absorption and emission of photons by certain types of matter.

22. The apparatus of claim 21, wherein the certain types of matter include living tissue.

23. The apparatus of claim 22, wherein the living tissue includes cancer cells.

24. The apparatus of claim 23, wherein the living tissue includes abnormal cells.

25. The apparatus of claim 14, wherein the image includes pixels that correspond to reflected colors of reflected photons and a false color assigned to emitted photons.

26. The apparatus of claim 25, wherein, for each pixel of the image, the reflected photons and the emitted photons come from the same portion within the area.

27. An apparatus for obtaining images, comprising:
a first light directing element operable to scan a first light including a first wavelength over an area, wherein the first wavelength is capable of inducing emission of a second wavelength from matter disposed in the area that is responsive to the first wavelength, wherein the first wavelength is different than the second wavelength;
a second light directing element operable to scan a second light over the area, wherein second light includes light corresponding to visible light to reflect from matter within the area;
a detector operable to detect emitted light including the second wavelength;
circuitry operable to attribute the emitted light including the second wavelength to a spot the first light was previously scanned over, wherein matter within the spot emitted the emitted light; and
circuitry operable to construct an image corresponding to reflected and emitted light that come from the area.

28. The apparatus of claim 27, wherein the matter that is responsive to the first wavelength is structured to absorb light including the first wavelength and emit the second wavelength, if emitted, after a predictable time interval when returning to a more stable state.

29. The apparatus of claim 27, wherein the matter that is responsive to the first wavelength comprises fluorescent matter.

30. The apparatus of claim 27, wherein the first light directing element is further operable to scan the first light over the area ahead of the second light scanned by the second light directing element such that emitted and reflected light from the spot arrive at the detector within a period corresponding to a sampling time.

31. The apparatus of claim 27, wherein the first and second light directing elements are operable to scan light over the area approximately in unison such that emitted light for the spot is detected after reflected light for the spot is detected.

32. The apparatus of claim 27, wherein the second light includes wavelengths corresponding to red, blue, and green.

33. The apparatus of claim 27, wherein the image includes pixels that correspond to reflected colors of reflected light and a false color assigned to emitted light.

34. A system for obtaining images, comprising:
a light directing element operable to scan light over an area, wherein the light is capable of inducing a fluorescent response from certain types of matter disposed in the area, and the light directing element is operable to scan to a new location within the area faster than the fluorescent response;
a detector operable to detect the fluorescent response; and
imaging circuitry operable to create an image based on a plurality of fluorescent responses and also based on information regarding orientations of the light directing element, wherein the orientations relate to the fluorescent responses.

35. The system of claim 34, wherein at least some of the fluorescent responses are received from different portions of the area.

36. The system of claim 34, wherein at least some of the fluorescent responses are received at different times.

37. The system of claim 34, wherein the image is part of a sequence of images that form a video of the area.

38. The system of claim 34, wherein the imaging circuitry is further operable to create the images at a rate of thirty images per second.

39. The system of claim 34, further comprising another light directing element operable to scan other light over the area, wherein the other light includes light having a greater probability of reflecting from matter within the area, wherein the imaging circuitry is further operable to create the image additionally based on light reflected from the area.

40. The system of claim 39, wherein the imaging circuitry is further operable to create the image by representing the plurality of fluorescent responses with a false color in pixels of the image that correspond to the fluorescent responses.

41. A method for obtaining images, comprising:
scanning a first light over a spot within an area, wherein the first light is scanned in a pattern in which the first light reaches most or all of the area;
after a period of time after the first light has scanned over the spot, detecting emitted light that is emitted from the spot; and
correlating the emitted light with the spot.

42. The method of claim 41, wherein correlating the emitted light with the spot comprises determining, according to the pattern, that the first light was directed to the spot based on the period of time and a speed at which the scanning occurs.

43. The method of claim 41, wherein the first light includes light that is capable of inducing certain matter disposed in the area to emit the emitted light.

44. The method of claim 43, wherein the certain matter is fluorescent matter.

45. The method of claim 43, wherein the certain matter includes living tissue.

46. The method of claim 45, wherein the living tissue is cancer cells.

47. The method of claim 45, wherein the living tissue is abnormal cells.

48. The method of claim 41, wherein detecting the emitted light is performed at a distance from the spot, and wherein the period of time is greater than the distance divided by a speed light travels over the distance.

49. The method of claim 41, wherein correlating the emitted light with the spot comprises:
scanning a second light over the area behind the scanning of the first light over the area such that the second light scans each spot the first light has scanned at approximately the period of time after the first light has scanned each spot;
detecting light that reflects from each spot as a result of the second light together with light that emits from each spot; and
collocating data corresponding to reflected light and emitted light.

50. The method of claim 41, wherein correlating the emitted light with the spot comprises storing data corresponding to the emitted light at an offset from data corresponding to light that reflects from the spot, wherein the offset corresponds to the period of time.

51. The method of claim 41, further comprising creating an image that attributes the emitted light to at least one pixel of the image, wherein the at least one pixel of the image corresponds to the spot.

52. The method of claim 51, wherein the emitted light has a frequency and is attributed to the at least one pixel by adding a false color representing the emitted light to the at least one pixel, wherein the false color corresponds to visible light having a different frequency than the frequency of the emitted light.

53. The method of claim 52, further comprising adding a reflected color to the at least one pixel based on light reflected from the spot.

54. The method of claim 41, further comprising attaching fluorescent material to a carrier that binds to material in the area, wherein the fluorescent material is responsive to the first light.

55. The method of claim 41, wherein the first light includes light that increases a probability of matter within the area reflecting the first light.

56. The method of claim 55, further comprising:
detecting reflected light that reflects from each spot; and
collocating data that corresponds to reflected light and emitted light.

57. An apparatus for obtaining images, comprising:
a light directing element operable to scan light over an area, wherein the light is capable of inducing light emissions from at least one type of matter disposed in the area;
a detector operable to detect emitted light that comes from a spot the light was previously scanned over, wherein the spot is within the area; and
means for attributing or correlating the emitted light to the spot.

* * * * *